US011066381B2

(12) United States Patent
Nakajima

(10) Patent No.: US 11,066,381 B2
(45) Date of Patent: Jul. 20, 2021

(54) UROLITHINS-CONTAINING AQUEOUS SOLUTION, DRIED SOLID COMPOSITION THEREOF AND PRODUCTION METHOD THEREFOR, AND UROLITHINS STABILIZING METHOD

(71) Applicant: DAICEL CORPORATION, Osaka (JP)

(72) Inventor: Takanori Nakajima, Myoko (JP)

(73) Assignee: DAICEL CORPORATION, Osaka (JP)

( * ) Notice: Subject to any disclaimer, the term of this patent is extended or adjusted under 35 U.S.C. 154(b) by 19 days.

(21) Appl. No.: 16/074,702

(22) PCT Filed: Feb. 1, 2017

(86) PCT No.: PCT/JP2017/003557

§ 371 (c)(1),
(2) Date: Aug. 1, 2018

(87) PCT Pub. No.: WO2017/135286

PCT Pub. Date: Aug. 10, 2017

(65) Prior Publication Data

US 2019/0040031 A1 Feb. 7, 2019

(30) Foreign Application Priority Data

Feb. 2, 2016 (JP) ............................ JP2016-018280

(51) Int. Cl.

| | |
|---|---|
| ***C07D 311/78*** | (2006.01) |
| ***A61K 8/65*** | (2006.01) |
| ***A61Q 19/00*** | (2006.01) |
| ***A61K 8/49*** | (2006.01) |
| ***A61K 47/42*** | (2017.01) |
| ***A61K 31/352*** | (2006.01) |
| ***C07K 14/78*** | (2006.01) |
| *A61K 9/08* | (2006.01) |

(52) U.S. Cl.

CPC ............ *C07D 311/78* (2013.01); *A61K 8/498* (2013.01); *A61K 8/65* (2013.01); *A61K 31/352* (2013.01); *A61K 47/42* (2013.01); *A61Q 19/00* (2013.01); *C07K 14/78* (2013.01); *A61K 9/08* (2013.01); *A61K 2800/10* (2013.01)

(58) Field of Classification Search

CPC .... C07D 311/78; A61K 31/352; A61K 47/42; A61K 8/498; A61K 8/65; A61K 9/08; A61K 2800/10; A61Q 19/00; C07K 14/78; A61P 9/00; A61P 39/06; A61P 3/10; A61P 3/06; A61P 3/04; A61P 3/00; A61P 29/00; A61P 25/28; A61P 25/22; A61P 25/00; A61P 21/00

See application file for complete search history.

(56) References Cited

U.S. PATENT DOCUMENTS

2009/0326057 A1* 12/2009 Seeram ................ A61K 31/195 514/460
2012/0164243 A1 6/2012 Rinsch et al.

FOREIGN PATENT DOCUMENTS

| | | | |
|---|---|---|---|
| CN | 102091057 A | * | 6/2011 |
| JP | 2002-027957 A | | 1/2002 |
| JP | 2010-001275 A | | 1/2010 |
| JP | 2010-168318 A | | 8/2010 |
| JP | 2012-077087 A | | 4/2012 |
| JP | 2014-501764 A | | 1/2014 |
| WO | WO 2008/111440 A1 | | 9/2008 |

OTHER PUBLICATIONS

CN 102091057. Published Jun. 15, 2011. Derwent abstract. (Year: 2011).*
Shi, X et al. The aggregation behavior of collagen in aqueous solution and its property of stabilizing liposomes in vitro. Biomaterials. 2001. 22: 1627-1634. (Year: 2001).*
Extended European Search Report dated Aug. 21, 2019, in European Patent Application No. 17747442.6.
English translation of International Preliminary Report on Patentability and Written Opinion dated Aug. 16, 2018, in PCT/JP2017/003557 (Forms PCT/IB/338, PCT/IB/373, and PCT/ISA/237).
Giménez-Bastida et al., “Intestinal Ellagitannin Metabolites Ameliorate Cytokine-Induced Inflammation and Associated Molecular Markers in Human Colon Fibroblasts”, Journal of Agricultural and Food Chemistry, vol. 60, No. 36, Sep. 12, 2012, pp. 8866-8876.
International Search Report (PCT/ISA/210) issued in PCT/JP2017/003557, dated Mar. 14, 2017.
Ishimoto et al., “Antioxidative Properties of Functional Polyphenols and Their Metabolites Assessed by an ORAC Assay”, Bioscience, Biotechnology, and Biochemistry, vol. 76, No. 2, 2012, pp. 395-399.
Ito et al., “Indentification of Urinary and Intestinal Bacterial Metabolites of Ellagitannin Geraniin in Rats”, Journal of Agricultural and Food Chemistry, vol. 56, 2008, pp. 393-400.
Nuñez-Sánchez et al., “Targeted metabolic profiling of pomegranate polyphenols and urolithins in plasma, urine and colon tissues from colorectal cancer patients”, Molecular Nutrition & Food Research, vol. 58, 2014, pp. 1199-1211.
Selma et al., “Description of urolithin production capacity from ellagic acid of two human intestinal *Gordonibacter* species”, Food & Function, vol. 5, Jun. 2014, pp. 1779-1784.
Selma et al., “*Gordonibacter urolithinfaciens* sp. nov., an urolithin-producing bacterium isolated from human gut”, International Journal of Systematic and Evolutionary Microbiology, vol. 64, 2014, pp. 2346-2352.
Verzelloni et al., “Antiglycative and neuroprotective activity of colon-deprived polyphenol catabolites”, Molecular Nutrition & Food Research, vol. 55, 2011, pp. S35-S43.
Written Opinion (PCT/ISA/237) issued in PCT/JP2017/003557, dated Mar. 14, 2017.

* cited by examiner

*Primary Examiner* — David W Berke-Schlessel
*Assistant Examiner* — Susan E. Fernandez
(74) *Attorney, Agent, or Firm* — Birch, Stewart, Kolasch & Birch, LLP

(57) ABSTRACT

A urolithin-containing aqueous solution containing urolithin and collagen, a dried solid composition thereof, methods for producing these, and a stabilization method for urolithin.

10 Claims, No Drawings

UROLITHINS-CONTAINING AQUEOUS SOLUTION, DRIED SOLID COMPOSITION THEREOF AND PRODUCTION METHOD THEREFOR, AND UROLITHINS STABILIZING METHOD

TECHNICAL FIELD

The present invention relates to a urolithin-containing aqueous solution, a dried solid composition thereof, methods for producing these, and a stabilization method for urolithin.

BACKGROUND ART

Urolithins represented by urolithin A are known to be metabolites of ellagic acid derived from ellagitannin contained in pomegranate, raspberry, blackberry, cloudberry, strawberry, walnut, and the like. Ellagitannin is classified as hydrolyzable tannin, and known to be hydrolyzed in the body after ingestion, to be converted into ellagic acid.

It is said that ellagitannin and ellagic acid show very low intestinal absorbability in the body. They are known to undergo, after ingestion, metabolism by the human colonic microbial flora to be converted into urolithins. The thus produced urolithins are among the most important compounds in the living body. In recent years, *Gordonibacter urolithinfaciens* has been reported as an enteric bacterium that produces urolithins (Non-patent Document 1).

Regarding production of urolithins in the living body, production of urolithins as metabolites of ellagitannin in the living body has been reported by a test using rats, wherein ellagitannin such as geraniin was given followed by analysis of urinary urolithins (Non-patent Document 2). Non-patent Document 3 reports that, in human, urolithin analogs are detected in urine after ingestion of a pomegranate extract containing ellagitannin composed mainly of punicalagin, and that, in particular, urolithin A functions as a major metabolite. Urolithin A has been reported to have a variety of effective actions such as an antioxidant action (Non-patent Document 4), anti-inflammatory action (Non-patent Document 5), and anti-saccharification action (Non-patent Document 6). In addition, foods, nutrition supplements, and the like containing urolithins for treatment or prevention of a symptom(s) selected from the group consisting of obesity, slow-down of metabolism, metabolic syndrome, diabetes, cardiovascular diseases, hyperlipidemia, neurodegenerative diseases, cognition disorders, mood disorders, stresses, and anxiety disorders, for body weight control, or for improvement of the muscle function or the mental capacity, have been reported (Patent Document 1). Thus, addition of urolithins to cosmetics, foods, raw materials of pharmaceuticals, processed products thereof, and the like has been demanded.

Conventionally, for the purpose of stably including such effective components in preparations, various stabilization methods such as a method in which a chelating agent is used for preservation of reduced coenzyme Q10 (Patent Document 2), a method in which astaxanthin is stabilized using cyclodextrin (Patent Document 3), and a method in which ascorbic acid is used for preservation of polyphenols (Patent Document 4) have been studied. However, no method has been reported for stable inclusion of urolithins in preparations. More specifically, there has been no satisfactory method from the viewpoint of stabilizing urolithins that are known to have useful effects, and maintaining the effects for a long period.

PRIOR ART DOCUMENTS

Patent Documents

[Patent Document 1] JP 2014-501764 A
[Patent Document 2] WO 2008/111440
[Patent Document 3] JP 2012-077087 A
[Patent Document 4] JP 2010-168318 A

Non-Patent Documents

[Non-patent Document 1] Int. J. Syst. Eval. Microbiol., 64, 2346-2352 (2014)
[Non-patent Document 2] J. Agric. Food Chem. 56, 393-400 (2008)
[Non-patent Document 3] Mol. Nutr. Food Res. 58, 1199-1211 (2014)
[Non-patent Document 4] Biosci. Biotechnol. Biochem. 76, 395-399 (2012)
[Non-patent Document 5] J. Agric. Food Chem. 60, 8866-8876 (2012)
[Non-patent Document 6] Mol. Nutr. Food Res. 55, S35-S43 (2011)

SUMMARY OF THE INVENTION

Problems to be Solved by the Invention

An object of the present invention is to provide a urolithin-containing aqueous solution, a dried solid composition thereof, methods for producing these, and a stabilization method for urolithin.

Means for Solving the Problems

In order to solve the problem described above, the present inventors intensively studied to discover that collagen has an action to improve stability of urolithins, thereby completing the present invention. The present invention is as follows.

<1> A urolithin-containing aqueous solution containing urolithin and collagen.

<2> The aqueous solution according to <1>, wherein the total amount of collagen is 0.1 to 100,000 parts by weight with respect to a total amount of 1 part by weight of urolithin.

<3> The aqueous solution according to <1> or <2>, wherein the urolithin is urolithin A.

<4> A dried solid composition of the aqueous solution according to any one of <1> to <3>.

<5> A method for producing a urolithin-containing aqueous solution, the method comprising: a blending step of blending urolithin with collagen.

<6> The production method according to <5>, wherein the collagen is at least one selected from the group consisting of type I collagen, type II collagen, type III collagen, type IV collagen, and type V collagen.

<7> The production method according to <5> or <6>, wherein the urolithin is urolithin A.

<8> The production method according to any one of <5> to <7>, wherein the total amount of collagen is 0.1 to 100,000 parts by weight with respect to a total amount of 1 part by weight of urolithin.

<9> A method for producing a dried solid composition of a urolithin-containing aqueous solution, the method comprising: a blending step of blending urolithin with collagen; and a drying step of drying the urolithin-containing aqueous solution obtained by the blending step.
<10> A stabilization method for urolithin in a urolithin-containing aqueous solution, the method comprising: a blending step of blending urolithin with collagen.
<11> The stabilization method according to <10>, wherein the urolithin is urolithin A.
<12> The stabilization method according to <10> or <11>, wherein the total amount of collagen is 0.1 to 100,000 parts by weight with respect to a total amount of 1 part by weight of urolithin.

Effect of the Invention

Urolithins are substances that exert effects such as anti-oxidation, anti-inflammation, and anti-saccharification, and can be expected to be effective for prevention of aging and wrinkles of the skin, whitening of the skin, and prevention of symptoms such as metabolic syndrome and diabetes.

According to the present invention, a urolithin-containing aqueous solution, a dried solid product thereof, and methods for producing these, wherein the stability of urolithin having such useful effects is remarkably improved, can be provided by use of collagen. In addition, a stabilization method for urolithin can be provided. The urolithin-containing aqueous solution containing a high concentration of stable urolithin or the dried solid product thereof can be used for providing cosmetics, quasi drugs, medical products, sanitary articles, pharmaceuticals, foods, supplements, and the like.

MODE FOR CARRYING OUT THE INVENTION

The present invention includes a first invention related to a urolithin-containing aqueous solution, a second invention related to a dried solid composition of the urolithin-containing aqueous solution, a third invention related to a method for producing a urolithin-containing aqueous solution, a fourth invention related to a method for producing a dried solid composition of a urolithin-containing aqueous solution, and a fifth invention related to a stabilization method for urolithin.

1. First Invention

The first invention of the present invention is a urolithin-containing aqueous solution containing urolithin and collagen.

(Urolithins)

The urolithin-containing aqueous solution according to the first invention of the present invention contains urolithin. The urolithin is not limited, and is a substance whose structure is represented by the following General Formula (1). As shown in Table 1, examples of the urolithin include urolithin A, urolithin B, urolithin C, urolithin D, urolithin E, urolithin M3, urolithin M4, urolithin M5, urolithin M6, urolithin M7, and isourolithin A, which vary in R1 to R6 in the chemical formula. A single kind of urolithin may be used, or two or more kinds of urolithins may be used in combination.

Among these, urolithin A is preferred since better improvement of stability can be achieved when it is present together with collagen.

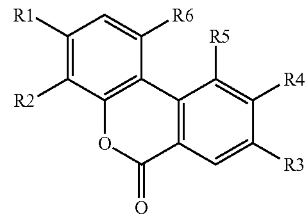

(1)

TABLE 1

| Type of urolithins | | | | | | |
|---|---|---|---|---|---|---|
| | R 1 | R 2 | R 3 | R 4 | R 5 | R 6 |
| Urolithin A | —OH | —H | —OH | —H | —H | —H |
| Urolithin B | —OH | —H | —H | —H | —H | —H |
| Urolithin C | —OH | —H | —OH | —OH | —H | —H |
| Urolithin D | —OH | —OH | —OH | —OH | —H | —H |
| Urolithin E | —OH | —OH | —OH | —H | —OH | —H |
| Urolithin M3 | —OH | —H | —OH | —OMe | —H | —H |
| Urolithin M4 | —OH | —H | —OMe | —OH | —H | —H |
| Urolithin M5 | —OH | —OH | —OH | —OH | —OH | —H |
| Urolithin M6 | —OH | —H | —OH | —OH | —OH | —H |
| Urolithin M7 | —OH | —H | —OH | —H | —OH | —H |
| Isourolithin A | —OH | —H | —H | —OH | —H | —H |

The method for obtaining the urolithin is not limited. A commercially available urolithin may be used, or the urolithin may be synthesized by chemical synthesis. Examples of commercially available urolithins include urolithin A, urolithin B, urolithin C, and urolithin D (manufactured by Dalton Pharma).

The synthesis method by chemical synthesis may be carried out according to a conventional method, and examples of the synthesis method include a method in which 2-bromo-5-methoxybenzoic acid and aluminum chloride are used as raw materials as described in Examples in the present description.

Alternatively, punicalagin, which is an ellagitannin, may be extracted from a plant followed by its hydrolysis into ellagic acid, or ellagic acid may be extracted, and then the ellagic acid may be converted to urolithin using a microorganism.

The type of the plant is not limited, and examples of the plant include pomegranate, raspberry, blackberry, cloudberry, boysenberry, strawberry, walnut, and geranium herb. Among these, pomegranate, boysenberry, and geranium herb are preferred since these contain a large amount of ellagitannin and/or ellagic acid. Pomegranate is more preferred.

A single kind of plant may be used, or two or more kinds of plants may be used in combination. The method for the extraction from the plant and the extraction conditions therefor are not limited, and the extraction may be carried out according to a conventional method. For example, a known extraction method such as water extraction, hot water extraction, warm water extraction, alcohol extraction, or supercritical extraction may be used.

In cases where solvent extraction is carried out, examples of the solvent include water; alcohols such as lower alcohols including methanol and ethanol, and polyols including propylene glycol and 1,3-butylene glycol (either anhydrous or aqueous); ketones such as acetone; diethyl ether; dioxane; acetonitrile; esters such as ethyl acetate; and xylene. The solvent is preferably water, ethanol, or the like. One of these solvents may be used, or two or more of these solvents may be used in combination.

The method for hydrolyzing the extracted ellagitannin such as punicalagin into ellagic acid is not limited, and examples of the method include methods in which the hydrolysis is carried out using an acid, enzyme, or microorganism.

The method for converting ellagic acid into urolithin using a microorganism is not limited. For example, a known method described in Food Funct., 5, 8, 1779-1784 (2014) may be used.

The urolithin obtained may be used as it is, or may be used in a powder state after drying. If necessary, the urolithin obtained may be subjected to purification, concentration treatment, or the like. As the purification treatment, treatment by filtration, or treatment by adsorption or decoloration using an ion-exchange resin, an activated carbon column, or the like may be carried out. As the concentration treatment, a conventional method using an evaporator or the like may be used.

The urolithin obtained (purification treatment product or concentrate) may be pulverized according to a known method such as a method in which the urolithin is subjected to freeze-drying treatment to achieve pulverization, or a method in which an excipient such as dextrin, corn starch, or gum arabic is added to the urolithin, followed by performing spray drying to achieve pulverization. Further, the resulting powder may be dissolved in pure water, ethanol, or the like, if necessary.

(Collagen)

The urolithin-containing aqueous solution, which is the first invention of the present invention, contains collagen.

Various kinds of collagens are known. Examples of the known collagens include type I to type V collagens. The type of the collagen in the first invention of the present invention is not limited as long as a desired effect can be exerted. A single kind of collagen may be used, or two or more kinds of collagens may be used in combination.

A derivative or the like of the collagen may also be used. The origin of the collagen is not limited, and the collagen may be any of an animal-derived collagen, a microorganism-derived collagen, or a synthetic product. The extraction method and the purification method for the collagen are not limited, and may be carried out according to known methods. A commercially available collagen may be used, and examples of such a collagen include collagen manufactured by Hanamai.

(Urolithin-Containing Aqueous Solution)

The urolithin-containing aqueous solution according to the first invention of the present invention contains urolithin and collagen as indispensable components, and other components may also be contained therein. The components other than urolithin and collagen are not limited as long as the effect of the first invention of the present invention can be exerted. For example, such components may be selected depending on the intended use. As described later, examples of the intended use include cosmetics, quasi drugs, medical products, sanitary articles, pharmaceuticals, foods, and supplements.

The content of urolithin with respect to the total amount of the urolithin-containing aqueous solution according to the first invention of the present invention is not limited as long as a desired effect can be exerted. The total content of urolithin is usually not less than 0.0001% by weight, preferably not less than 0.0005% by weight, more preferably not less than 0.001% by weight. On the other hand, the total content is usually not more than 10% by weight, preferably not more than 1% by weight, more preferably not more than 0.1% by weight.

The content of collagen with respect to the total amount of the urolithin-containing aqueous solution according to the first invention of the present invention is not limited as long as a desired effect can be exerted. The total content of collagen is usually not less than 0.01% by weight, preferably not less than 0.05% by weight, more preferably not less than 0.1% by weight. On the other hand, the total content is usually not more than 70% by weight, preferably not more than 20% by weight, more preferably not more than 5% by weight.

When appropriate, the urolithin-containing aqueous solution may contain, in addition to urolithin and collagen, for example, a known component that is commonly used as a material of cosmetics. Examples of such a known component include ethanol and glycerin. The content of such a known component is also not limited, and may be within a range that is normally used.

(Stability of Urolithin)

From the viewpoint of improvement of the stability of urolithin, collagen is contained in a total amount of usually not less than 0.1 parts by weight, preferably not less than 1 part by weight, more preferably not less than 10 parts by weight, still more preferably not less than 100 parts by weight, with respect to a total amount of 1 part by weight of urolithin in the urolithin-containing aqueous solution. On the other hand, the total amount of collagen is usually not more than 100,000 parts by weight, preferably not more than 50,000 parts by weight, more preferably not more than 20,000 parts by weight, still more preferably not more than 10,000 parts by weight.

In cases where collagen is present in a total amount of usually not less than 0.1 parts by weight, preferably not less than 1 part by weight, more preferably not less than 10 parts by weight, still more preferably not less than 100 parts by weight with respect to a total amount of 1 part by weight of urolithin, stabilization of the urolithin tends to be found, and the urolithin tends to be stabilized in a concentration-dependent manner. On the other hand, as the amount of collagen decreases, an advantage increases from the viewpoint of ease of handling during formulation, and reduction of impact on the formulation.

The stability of urolithin can be studied by measuring the total amount of urolithin before storage and the total amount of urolithin after storage under a temperature condition of 60° C. for one week or two weeks, and then calculating the urolithin residual ratio (%) according to the following calculation equation. As the method for measuring urolithin, for example, the method using HPLC described in Examples can be used.

$$\text{Urolithin residual ratio (\%)} = (\text{total amount of urolithin after storage}/\text{total amount of urolithin before storage}) \times 100 \quad \text{[Calculation Equation]}$$

Regarding the stability of urolithin, the urolithin residual ratio (%) after one week of storage is preferably not less than 70%, more preferably not less than 80%, still more preferably not less than 90%. The urolithin residual ratio (%) after two weeks of storage is preferably not less than 50%, more preferably not less than 70%, still more preferably not less than 80%.

(Use of Urolithin-Containing Aqueous Solution)

The urolithin-containing aqueous solution according to the first invention of the present invention may be used for cosmetics, quasi drugs, medical products, sanitary articles, pharmaceuticals, foods, supplements, and the like. By the action of urolithin, an effect(s) such as anti-oxidation, anti-inflammation, and/or anti-saccharification can be expected to be produced.

The aqueous solution may contain only urolithin and collagen, or may contain, besides these components, known excipients, perfumes, coloring agents, emulsifiers, stabilizers, thickeners, enzymes, antiseptics, antimicrobial agents, lubricants, surfactants, disintegrators, disintegration suppressing agents, binders, absorption enhancers, adsorbents, humectants, solubilizers, preservatives, flavoring agents, sweetening agents, ultraviolet absorbers, and the like as long as the effects described above are not deteriorated.

(Cosmetics)

When the urolithin-containing aqueous solution according to the first invention of the present invention is used as a material of cosmetics, it may be prepared into a variety of desired formulations such as liquid formulations including aqueous solutions, lotions, sprays, suspensions, and emulsions; solid formulations including powders, granules, and blocks; semisolid formulations including creams and pastes; and gel formulations.

More specifically, the urolithin-containing aqueous solution may be used for toilet soaps, shampoos, facial cleansers, hair conditioners, eye creams, eye shadows, creams/milky lotions, face lotions, beauty lotions, perfumes, face powders, cosmetic oils, hair cosmetics, hair dyes, solid perfumes, powders, facial masks, cleansing creams, shaving creams, shaving lotions, tanning oils, sunscreen oils, tanning lotions, sunscreen lotions, tanning creams, sunscreen creams, foundations, powder perfumes, cheek rouges, mascaras, eyebrow pencils, nail creams, beauty nail enamels, beauty nail enamel removers, hair washing agents, bath cosmetics, lipsticks, lip creams, eye liners, tooth pastes, deodorants, colognes, hair restorers, hair-growing agents, and the like.

In cases where the aqueous solution is used as a material of a cosmetic, a variety of known components that are commonly used for cosmetics may be included depending on the purpose. Examples of such components that may be included include surfactants, lower alcohols, and polyols.

A cosmetic using the aqueous solution may be produced according to a conventional method. The amount of addition, the method of addition, and the timing of addition of the aqueous solution to the cosmetic may be appropriately selected. Further, if necessary, the resulting cosmetic may be enclosed in an appropriate container such as a bottle, bag, can, spray can, spray container, box, or pack.

In cases where the aqueous solution is used as a material of a cosmetic, the content of the aqueous solution with respect to the total amount of the cosmetic is not limited as long as the above effect can be exerted. The content of the aqueous solution in terms of the total amount of urolithin is usually not less than 0.0001% by weight, preferably not less than 0.0005% by weight, more preferably not less than 0.001% by weight. On the other hand, it is usually not more than 1% by weight, preferably not more than 0.1% by weight, more preferably not more than 0.05% by weight.

The content in terms of the total amount of collagen is usually not less than 0.0001% by weight, preferably not less than 0.001% by weight, more preferably not less than 0.01% by weight. On the other hand, it is usually not more than 10% by weight, preferably not more than 5% by weight, more preferably not more than 3% by weight.

The aqueous solution may also contain a humectant which is commonly used for cosmetics and which allows exertion of the effect of the first invention of the present invention. Examples of the humectant include proteins; mucopolysaccharides; sphingolipids; saccharoids and polyols such as sucrose, sorbitol, glycerin, 1,3-butylene glycol, propylene glycol, and dipropylene glycol; polyether-based compounds prepared by addition polymerization of 2 to 100 moles of propylene oxide and not more than 50 moles of ethylene oxide with a polyol core having not less than three hydroxyl groups in the molecule; ethyl gluceth-10; caronic acid; atelocollagen; cholesteryl-12-hydroxystearate; bile acid monosalt; dl-pyrrolidone carboxylic acid monosalt; short-chain soluble collagen; *Rosa roxburghii* extracts; *Achillea millefolium* extracts; glycols such as propylene glycol, dipropylene glycol, 1,3-butylene glycol, 1,4-butylene glycol, diethylene glycol, and triethylene glycol, and polyethylene glycols having molecular weights higher than their molecular weights; glycerin and diglycerin, and polyglycerins having molecular weights higher than their molecular weights; sugar alcohols such as sorbitol, mannitol, maltitol, xylitol, and erythritol; sugars such as fructose, glucose, galactose, maltose, lactose, and trehalose; and polypropylene glycol-polyethylene glycol copolymers and dimethyl ethers thereof. One of these may be used, or two or more of these may be used.

The humectant is preferably one or more selected from the group consisting of proteins, mucopolysaccharides, and sphingolipids. The humectant is more preferably a protein. The origin of the humectant is not limited, and the humectant may be any of an animal-derived humectant, a microorganism-derived humectant, or a synthetic product. The extraction method and the purification method for the humectant are not limited, and may be carried out according to known methods.

The protein is not limited, and examples of the protein include elastin, keratin, and derivatives and salts thereof. The origin of the protein is not limited, and the protein may be any of an animal-derived protein, a microorganism-derived protein, or a synthetic product. The extraction method and the purification method for the protein are not limited, and may be carried out according to known methods.

The mucopolysaccharide is not limited, and examples of the mucopolysaccharide include hyaluronic acid, mucoitin sulfate, chondroitin sulfate, dermatan sulfate, heparan sulfate, heparin, and keratan sulfate, and salts thereof. The origin of the mucopolysaccharide is not limited, and the mucopolysaccharide may be any of an animal-derived mucopolysaccharide, a microorganism-derived mucopolysaccharide, or a synthetic product, similarly to the above cases. The extraction method and the purification method for the mucopolysaccharide are not limited, and may be carried out according to known methods.

Sphingolipid is a general term for lipids having a sphingo base (sphingosine or dihydrosphingosine) in the basic skeleton. The sphingolipid is not limited, and examples of the sphingolipid include sphingosine, ceramide, sphingoglycolipid, and sphingophospholipid. The sphingoglycolipid is not limited, and examples of the sphingoglycolipid include galactosyl cerebroside, lactosyl cerebroside, and ganglioside. The sphingophospholipid is not limited, and examples of the sphingophospholipid include long-chain bases and long-chain fatty acids such as sphingosine and phytosphingosine; and ceramide 1-phosphate derivatives (for example, sphingomyelin) and ceramide 1-phosphonate derivatives (for example, ceramide aminoethylphosphonate) having phosphoric acid or phosphonic acid. The origin of the sphingolipid is not limited, and the sphingolipid may be any of an animal-derived sphingolipid, a microorganism-derived sphingolipid, or a synthetic product, similarly to the above cases. The extraction method and the purification method for the sphingolipid are not limited, and may be carried out according to known methods.

Known components that are commonly used for cosmetics, some of which are already described above, may be further added as appropriate. Examples of such components include:

natural and synthetic surfactants such as anionic surfactants (fatty acid soaps, sulfonate-type anionic surfactants, sulfate-type anionic surfactants, phosphate-type anionic surfactants, acylmethyl taurine salt, monoalkyl phosphates, acylglutamate, isethionic acid ester salt, and the like); cationic surfactants (amine salt-type cationic surfactants and quaternary ammonium-type cationic surfactants (tetraalkylammonium-type and pyridinium-type)); nonionic surfactants (glycerin fatty acid esters, propylene glycol fatty acid esters, sorbitan fatty acid esters, polyoxyethylene sorbitan fatty acid esters, tetraoleic acid polyoxyethylene sorbitol, polyoxyethylene alkyl ethers, polyoxyethylene polyoxypropylene glycols, polyoxyethylene polyoxypropylene alkyl ethers, polyethylene glycol fatty acid esters, polyoxyethylene castor oils, polyoxyethylene hydrogenated castor oils, polyglycerin fatty acid esters, and the like); amphoteric surfactants (imidazoline-type, betaine-type, and amino acid-type); fluorine-based surfactants; and silicone-based surfactants;

water-soluble polymers such as sodium alginate, alginic acid propylene glycol esters, gum arabic, xanthan gum, pectin, tragacanth, sodium carboxymethylcellulose, methyl cellulose, carboxyvinyl polymers, polyethylene glycol, polyvinyl alcohol, polyvinyl pyrrolidone, cationized cellulose, cationized dextran, cationized dextrin, chitosan, cationized vinylpyrrolidone polymers, N,N-dimethyl-3,5-methylenepiperidinium chloride polymers, milk protein, soy protein, gelatin, egg protein, casein sodium, and whey protein;

components of plants such as ginkgo, *Centella asiatica* (tubokusa), *Swertia japonica* (touyaku), *ginseng, Lycium* bark (sikoppi), *Sophora japonica* flower (kaika), *Artemisia capillaris* flower (intikou), *Alnus firma* fruit (yashajitu), glycyrrhiza fractions, *Acanthopanax/Periploca* sepium bark (gokahi), Inula britannica flower (senpukuka), *Dioscorea tokoro* (hikai), *Daphniphyllum macropodum* (yuzuriha), *Matricaria recutita* (kamiture), horse chestnut, escin, *Terminalia*, ruscogenin, butcher's bloom, kola, guarana, mate, coffee, cacao, Plectranthus, *Salvia miltiorrhiza* (tanjin), visnaga, silymarin, leucocyanin, *Hypericum erectum*, kumahaze, *Perilla, Scutellaria* root (ougon), *Schizonepeta* spike (keigai), rosemary, sage, thyme, mugwort, *Artemisia capillaris, Atractylodes lancea* rhizome (soujutu), *Achillea millefolium, Lithospermum* root (sikon), fennel, *Phellodendron* bark (oubaku), ginger, *Angelica acutiloba* root (touki), *Cnidium* rhizome (senkyu), *Citrus unshiu* peel (chinbi), *Valeriana fauriei, Angelica dahurica* root (byakusi), bitter orange peel, peony root, safflower, sweet flag, *Poria sclerotium* (bukuryou), and peppermint;

active components such as succinic acid, fumaric acid, citric acid, pyruvic acid, glucuronic acid, 2-hydroxybutyric acid, lactic acid, malic acid, tartaric acid, tartronic acid, methyl pyruvate, ethyl pyruvate, vitamin A acid, vitamin C derivatives, vitamin D, vitamin E, oligopeptides, and tranexamate;

humectants such as polyols, amino acids, mucopolysaccharides, proteins, biological extracts, fermentation metabolites, polysaccharides, plant extracts, phospholipids, and ceramide;

fat/oil components (emollient ingredients) such as fats and oils (natural fats and oils including soy oil, bran oil, jojoba oil, avocado oil, almond oil, cacao oil, olive oil, sesame oil, persic oil, castor oil, palm oil, mink oil, beef tallow, and lard; hardened oils obtained by hydrogenation of these natural fats and oils; synthetic triglycerides and diglycerides such as myristic acid glyceride and 2-ethylhexanoic acid glyceride; and the like); waxes (carnauba wax, spermaceti, beeswax, lanolin, and the like); hydrocarbons (liquid paraffin, vaseline, paraffin, microcrystalline wax, ceresin, squalane, pristane, and the like); higher fatty acids (lauric acid, myristic acid, palmitic acid, stearic acid, behenic acid, oleic acid, linoleic acid, linolenic acid, lanolic acid, isostearic acid, and the like); higher alcohols (lauryl alcohol, cetyl alcohol, stearyl alcohol, oleyl alcohol, cholesterol, 2-hexyldecanol, and the like); esters (cetyl octanoate, myristyl lactate, cetyl lactate, isopropyl myristate, myristyl myristate, isopropyl palmitate, isopropyl adipate, butyl stearate, decyl oleate, cholesteryl isostearate, and the like); essential oils (mentha oil, jasmine oil, camphor oil, Japanese cypress oil, bitter orange oil, ryu oil, turpentine oil, cinnamon oil, bergamot oil, mandarin orange oil, calamus oil, pine oil, lavender oil, bay oil, clove oil, hiba oil, rose oil, eucalyptus oil, lemon oil, peppermint oil, thyme oil, rose oil, sage oil, menthol, cineole, eugenol, citral, citronellal, borneol, linalool, geraniol, camphor, thymol, spilanthol, pinene, limonene, terpenoid compounds, and the like); and silicone oils;

inorganic salts such as sodium carbonate, sodium hydrogen carbonate, sodium sesquicarbonate, borax, sodium sulfate, sodium sulfide, sodium nitrate, sodium thiosulfate, sodium polyphosphate, sodium phosphate, potassium chloride, potassium sulfide, calcium oxide, magnesium oxide, calcium carbonate, and magnesium carbonate;

inorganic acids such as boric acid, metasilicic acid, and silicic anhydride;

dyes such as Yellow No. 4, Blue No. 1, Yellow No. 202, chlorophyll, riboflavin, safflower, crocin, and anthraquinone;

perfumes;

polymers such as acrylic resins, styrene resins, epoxy resins, nylon, polyethylene, polypropylene, polyvinyl chloride, polyethylene terephthalate resins, and polytetrafluoroethane; copolymers of these polymers; and fine powders of silicic acid, calcium silicate, natural aluminum silicate, synthetic aluminum silicate, zeolite, titanium oxide, talc, kaolin, mica, or bentonite;

sulfur, sinter, mineral sand, mica powder, neutral white clay, roasted rice bran, microbicides, and antiseptics; and other components necessary for the formulation.

(Quasi Drugs, Medical Products, Sanitary Articles, Pharmaceuticals)

The urolithin-containing aqueous solution according to the first invention of the present invention may be used as a material for quasi drugs, medical products, sanitary articles, and pharmaceuticals. All of these may be for either external use or internal use. In these cases, the urolithin-containing aqueous solution may be prepared into a variety of desired formulations such as liquid formulations including aqueous solutions, lotions, sprays, suspensions, and emulsions; solid formulations including powders, granules, and blocks; semi-solid formulations including creams and pastes; and gel formulations.

Specific examples of the formulations include basic cosmetics such as ointments, poultices, face lotions, milky lotions, creams, salves, lotions, oils, and facial masks; facial cleansers and skin cleansers; hair cosmetics such as shampoos, hair conditioners, hair treatment agents, hair creams, pomades, hair sprays, hair dressings, permanent wave agents, hair tonics, hair dyes, hair-growing agents, and hair restorers; makeup cosmetics such as foundations, white makeup powders, face powders, lipsticks, cheek rouges, eye shadows, eye liners, mascaras, eyebrow pencils, and eyelashes; finishing cosmetics such as beauty nail agents; perfumes; bath agents; and further, tooth pastes, mouth fresheners/gargles, liquid odor-deodorizing/preventing agents, sanitary articles, sanitary cottons, and wet tissues.

These quasi drugs, medical products, sanitary articles, and pharmaceuticals may be produced according to conventional methods using, if necessary, known auxiliary agents that can be normally used in the art, such as fillers, bulking agents, excipients, binders, humectants, disintegrators, surfactants, lubricants, coloring agents, correctives, solubilizers, suspending agents, and coating agents. These may also contain coloring agents, preservatives, perfumes, flavoring agents, sweetening agents, and the like, and other quasi drugs, medical products, sanitary articles, and pharmaceuticals.

In cases where the aqueous solution is used as a material of a quasi drug, medical product, sanitary article, or pharmaceutical, a variety of known components and additives that are commonly used for these may also be contained. Examples of such components and additives that may be contained include higher alcohols; silicone; waxes; oils; alcohols; esters; metallic soaps; gummy matters; water-soluble polymer compounds; surfactants; vitamins; amino acids; extraction products and extracts from animals, plants, and crude drugs; microorganism culture metabolites such as yeast extract; pigments; astringents; microbicides/disinfectants; perfumes; dyes/coloring agents; sweetening agents; hormones; sequestering agents; pH adjusters; chelating agents; antiseptic/antifungal agents; refrigerants; stabilizers; emulsifiers; animal/plant proteins and degradation products thereof; animal/plant polysaccharides and degradation products thereof; animal/plant glycoproteins and degradation products thereof; blood flow promoters; anti-inflammatory agents/antiallergic agents; cell-activating agents; keratolytic agents; wound healing agents; foam-increasing agents; thickeners; agents for the oral cavity; deodorants; bittering agents; seasonings; and enzymes.

Although the aqueous solution is preferably applied to human, it may also be applied to non-human animals as long as the effect of the first invention of the present invention can be exerted.

In cases where the aqueous solution is used as a material of a quasi drug, medical product, sanitary article, or pharmaceutical, the content of the aqueous solution with respect to the total amount of each of these is not limited as long as the above effect can be exerted. The content of the aqueous solution in terms of the total amount of urolithin is usually not less than 0.0001% by weight, preferably not less than 0.0005% by weight, more preferably not less than 0.001% by weight. On the other hand, it is usually not more than 1% by weight, preferably not more than 0.1% by weight, more preferably not more than 0.05% by weight. The content in terms of the total amount of collagen is usually not less than 0.0001% by weight, preferably not less than 0.001% by weight, more preferably not less than 0.01% by weight. On the other hand, it is usually not more than 10% by weight, preferably not more than 5% by weight, more preferably not more than 3% by weight.

(Foods)

In cases where the urolithin-containing aqueous solution according to the first invention of the present invention is used as a material of a food, the aqueous solution may be used not only for a common food, but also for a food for specified health use, dietary supplement, functional food, food for patients, food additive, or the like. Examples of the form of the food include soft drink, milk, pudding, jelly, candy, chewing gum, gummy candy, yogurt, chocolate, soup, cookie, snack, ice cream, ice candy, bread, cake, cream puff, ham, meat sauce, curry, stew, cheese, butter, and dressing containing the aqueous solution.

The aqueous solution may contain, as a major component, water, protein, carbohydrate, lipid, vitamin, mineral, organic acid, organic base, juice, flavor, or the like. Examples of the protein include animal and plant proteins such as whole milk powder, skimmed milk powder, semi-skimmed milk powder, casein, soy protein, chicken egg protein, and meat protein; hydrolysates thereof; and butter. Examples of the carbohydrate include sugars, processed starches (dextrin, soluble starch, British starch, oxidized starch, starch ester, starch ether, and the like), and dietary fibers. Examples of the lipid include lard; and vegetable oils and fats such as safflower oil, corn oil, rapeseed oil, and palm oil, and fractionated oils, hydrogenated oils, and transesterified oils thereof. Examples of the vitamin include vitamin A, carotenes, vitamin Bs, vitamin C, vitamin Ds, vitamin E, vitamin Ks, vitamin P, vitamin Q, niacin, nicotinic acid, pantothenic acid, biotin, inositol, choline, and folic acid; and examples of the mineral include calcium, potassium, magnesium, sodium, copper, iron, manganese, zinc, selenium, and whey minerals. Examples of the organic acid include malic acid, citric acid, lactic acid, and tartaric acid. Two or more of these components may be used in combination. A synthetic product(s) and/or a food(s) containing these in a large amount may also be used.

In cases where the aqueous solution is used as a material of a food, the food may be produced according to a conventional method. The amount of addition, the method of addition, and the timing of addition of the aqueous solution to the food may be appropriately selected. Further, if necessary, the resulting food may be enclosed in an appropriate container such as a bottle, bag, can, box, or pack.

In cases where the aqueous solution is used as a material of a food, the content of the aqueous solution with respect to the total amount of the food is not limited as long as the above effect can be exerted. The content of the aqueous solution in terms of the total amount of urolithin is usually not less than 0.0001% by weight, preferably not less than 0.0005% by weight, more preferably not less than 0.001% by weight. On the other hand, it is usually not more than 10% by weight, preferably not more than 1% by weight, more preferably not more than 0.1% by weight. The content in terms of the total amount of collagen is usually not less than 0.01% by weight, preferably not less than 0.05% by weight, more preferably not less than 0.1% by weight. On the other hand, it is usually not more than 70% by weight, preferably not more than 20% by weight, more preferably not more than 5% by weight.

(Supplements)

Supplements are classified into a group of food composed of dietary supplements. In the present description, a supplement means a functional auxiliary substance that can provide anti-oxidation, anti-inflammation, anti-saccharification, and/or the like.

In cases where the urolithin-containing aqueous solution according to the first invention of the present invention is used as a material of a supplement, the supplement may be prepared in the form of any of a solid product, gelatinous product, and liquid product. Examples of the form of the supplement include forms such as various processed foods and beverages, powders, tablets, balls, capsules, jellies, and granules.

In cases where the aqueous solution is used as a material of a supplement, the supplement may contain an additive, wherein examples of the additive include excipients such as dextrin; preservatives such as vitamin C; corrigents such as vanillin; dyes such as safflower dye; monosaccharides, oligosaccharides, and polysaccharides (for example, glucose, fructose, sucrose, saccharose, and carbohydrates containing these); acidulants; perfumes; fats and oils, emulsifiers; whole milk powder; and agar. Two or more of these components may be used in combination. A synthetic product(s) and/or these may be contained in a large amount.

In cases where the aqueous solution is used as a material of a supplement, the supplement may be produced according to a conventional method. The amount of addition, the method of addition, and the timing of addition of the aqueous solution to the supplement may be appropriately selected. Further, if necessary, the resulting supplement may be enclosed in an appropriate container such as a bottle, bag, can, box, or pack.

In cases where the aqueous solution is used as a material of a supplement, the content of the aqueous solution with respect to the total amount of the supplement is not limited as long as the above effect can be exerted. The content of the aqueous solution in terms of the total amount of urolithin is usually not less than 0.0001% by weight, preferably not less than 0.0005% by weight, more preferably not less than 0.001% by weight. On the other hand, it is usually not more than 10% by weight, preferably not more than 1% by weight, more preferably not more than 0.1% by weight. The content in terms of the total amount of collagen is usually not less than 0.01% by weight, preferably not less than 0.05% by weight, more preferably not less than 0.1% by weight. On the other hand, it is usually not more than 70% by weight, preferably not more than 20% by weight, more preferably not more than 5% by weight.

(Indications)

The cosmetics, quasi drugs, medical products, sanitary articles, pharmaceuticals, foods, supplements, and the like using the urolithin-containing aqueous solution according to the first invention of the present invention may be sold with an indication that they are intended for use in anti-oxidation, anti-inflammation, anti-saccharification, and/or the like.

The "indication" means any action to inform the above intended use(s) to consumers. Any indication that allows expectation or inference of the intended use(s) is the "indication" in the present invention irrespective of the purpose of the indication, the content of the indication, the object or the medium with which the indication is given, or the like. However, the indication is preferably given with an expression that allows a consumer to directly recognize the above intended use(s). Specific examples of the indication include actions of describing the above intended use(s) on an article related to a cosmetic, quasi drug, medical product, sanitary article, pharmaceutical, food, supplement, or the like, or on a wrapping of the article; actions of assignment, delivery, or display and import for the purpose of assignment or delivery, of an article or a wrapping of the article on which the above intended use(s) is/are described; and actions of describing the above intended use(s) in an advertisement, price list, or transaction document related to an article, and displaying or distributing these, or describing the above intended use(s) in information including these as a content, and providing it electromagnetically (through internet or the like).

The indication is preferably an indication approved by the government or the like (for example, an indication which is approved based on a system(s) established by the government, and which is carried out in a mode in accordance with such approval). The indication is especially preferably given to an advertisement material in a sales location, such as a wrapping, container, catalog, pamphlet, or POP, or to other documents.

In cases of a food using the aqueous solution according to the first invention of the present invention, examples of the indication include those for a health food, functional food, special purpose food, functional nutritional food, quasi drug, or the like, and those approved by the Ministry of Health, Labour and Welfare, such as the indication approved by the "food for specified health use" system or a system similar thereto. Examples of the latter indications include the indication for a food for specified health use, the indication for a conditional food for specified health use, an indication informing that a structure or a function of the body may be influenced, and an indication informing reduction of a disease risk. More specifically, typical examples of the indications may include the indication for a food for specified health use (in particular, indication of health uses) as specified in Enforcement Regulations of the Health Promotion Law (Ordinance No. 86 of the Ministry of Health, Labour and Welfare of Japan; Apr. 30, 2003).

2. Second Invention (Dried Solid Composition of Urolithin-containing Aqueous Solution)

The second invention of the present invention is a dried solid composition of the urolithin-containing aqueous solution according to the first invention of the present invention.

The drying of the urolithin-containing aqueous solution for preparation of the dried solid composition may be carried out by any process as long as a desired effect can be exerted. Examples of the drying method include, but are not limited to, methods using a known or commercially available droplet spray-type dryer such as a freeze dryer, spray dryer, or slurry dryer. Further, if necessary, the dried product may be subjected to a treatment(s) such as pulverization and/or classification, and/or may be, if necessary, subjected to a molding treatment such as granulation.

(Intended Uses of Dried Solid Composition of Urolithin-containing Aqueous Solution)

The dried solid composition may be used for a cosmetic, quasi drug, medical product, sanitary article, pharmaceutical, food, supplement, or the like. All of these may be for either external use or internal use. By the action of urolithin, an effect(s) such as anti-oxidation, anti-inflammation, and/or anti-saccharification can be expected to be produced.

The description of intended uses of the urolithin-containing aqueous solution in the description of the first invention of the present invention is applicable to the description of intended uses of the dried solid composition. Therefore, the description is omitted in this section.

3. Third Invention

The third invention of the present invention is a method for producing a urolithin-containing aqueous solution, the method comprising a blending step of blending urolithin with collagen. This production method indispensably includes the blending step of blending urolithin with collagen, but other steps may also be included.

(Blending Step)

The blending step is a step of blending urolithin with collagen. In the blending step, predetermined amounts of urolithin and collagen are blended to provide a urolithin-containing aqueous solution. In this process, urolithin and collagen are blended as indispensable components, but other components may also be blended. Regarding the amount of each component blended, the description given for the first invention of the present invention is applied.

The blending method in this step is not limited, and a known method may be used. After mixing the components, a treatment(s) such as stirring and/or heating may be carried out, if necessary. A commonly used device(s) such as a shaker, magnetic stirrer, mechanical stirrer, ultrasonic device, and/or homogenizer may be used therefor.

Regarding the temperature conditions in this step, the step is preferably carried out at a temperature at which the urolithin is not degraded. The temperature is preferably not less than 10° C., more preferably not less than 15° C., still more preferably not less than 20° C. On the other hand, the temperature is preferably not more than 80° C., more preferably not more than 60° C., still more preferably not more than 40° C.

Regarding other factors in the third invention, the description given for the first invention of the present invention is applied.

4. Fourth Invention

The fourth invention of the present invention is a method for producing a dried solid composition of a urolithin-containing aqueous solution, the method comprising: a blending step of blending urolithin with collagen; and a drying step of drying the urolithin-containing aqueous solution obtained by the blending step. This production method indispensably includes the blending step and the drying step, but other steps may also be included.

(Blending Step)

The blending step is a step of blending urolithin with collagen, and the description given for the third invention is applied thereto.

(Drying Step)

The drying step is a step of drying the urolithin-containing aqueous solution obtained in the blending step. The drying method is not limited, and the drying may be carried out using, for example, a known or commercially available droplet spray-type dryer such as a freeze dryer, spray dryer, or slurry dryer. In such cases, the drying temperature for the droplet spray-type dryer may be usually set to not more than 250° C., more preferably set to not more than 130° C. Further, if necessary, the dried product may be subjected to a treatment(s) such as pulverization and/or classification, and/or may be, if necessary, subjected to a molding treatment such as granulation.

3. Fifth Invention

The fifth invention of the present invention is a stabilization method for urolithin, the method comprising a blending step of blending urolithin with collagen. The stabilization method indispensably includes the blending step of blending urolithin with collagen, but other steps may also be included.

The blending step is a step of blending urolithin with collagen, and the description given for the third invention is applied thereto.

EXAMPLES

The present invention is described below in more detail by way of particular examples. However, the present invention is not limited to these examples.

(Method for Analyzing Urolithin)

A description is given below for a case where urolithin A was used as the urolithin. Analysis of urolithin A was carried out using HPLC. More specifically, urolithin A (manufactured by Dalton Farma) was dissolved in an appropriate solvent to prepare a solution, and the solution was analyzed under the following HPLC conditions. Using the purity (%) (A) and the peak area value (B) in the HPLC, the factor of urolithin A and the urolithin A concentration in the sample were calculated according to the following calculation equation (1) and calculation equation (2).

(Calculation Equation for Factor of Urolithin A)

$$\text{Factor of urolithin } A=(B)/(\text{concentration of standard solution of urolithin } A\ (\text{mg/L})\times(A)/100) \quad (1)$$

(Calculation Equation for Urolithin A Concentration in Sample)

$$\text{Urolithin } A \text{ concentration in sample (mg/L)}=\text{peak area value of urolithin } A \text{ in sample/factor of urolithin } A \quad (2)$$

(Analysis Conditions)

Analysis Column: Inertsil ODS-3 (250×4.6 mm) (manufactured by GL Science)

Detection Wavelength: 305 nm

Mobile phase: water/acetonitrile/acetic acid=74/25/1

Column temperature: 40° C.

Flow rate: 1.0 mL/min.

Under these conditions, urolithin A had a retention time of 16.5 minutes.

<Preparation of Urolithin A>

In 150 mL of chlorobenzene, 5 g of 2-bromo-5-methoxybenzoic acid (manufactured by Wako Pure Chemical Industries, Ltd.) and 15 g of aluminum chloride were refluxed for 2.5 hours. After cooling, the reaction liquid was transferred to ice water, and extraction was carried out using 250 mL of diethyl ether three times. The obtained extract was concentrated under reduced pressure to evaporate diethyl ether, to obtain 4.2 g of 2-bromo-5-hydroxybenzoic acid. In 9 mL of 4 M aqueous NaOH solution, 3.9 g of the obtained 2-bromo-5-hydroxybenzoic acid and 3.9 g of resorcinol (manufactured by Tokyo Chemical Industry Co., Ltd.) were heated at 60° C. for 30 minutes. To this reaction liquid, 1.8 mL of 10% aqueous copper sulfate solution was added, and heating was further carried out at 80° C. for 10 minutes. The resulting precipitate was collected by filtration to obtain white powder of urolithin A.

<Stability Improvement Test for Urolithin>

Example 1

To an aqueous solution containing 10% ethanol and 10% glycerin, urolithin A was added to a concentration of 0.005%, and then the urolithin A was dissolved therein. To this solution, collagen (Hanamai) was added to a concentration of 0.5% to prepare a urolithin A-containing aqueous solution. The urolithin A content in the urolithin A-containing aqueous solution was measured after one week of storage and after two weeks of storage under a temperature condition of 60° C. By comparing the urolithin A contents measured before and after the storage, the residual ratio was calculated to evaluate the stability.

Comparative Example 1

The same operation as in Example 1 was carried out except that collagen was not added, to provide a control as Comparative Example 1.

The residual ratio of urolithin A was calculated according to the following calculation equation (3).

$$\text{Urolithin residual ratio (\%)} = (\text{content of urolithin } A \text{ after storage/content of urolithin } A \text{ before storage}) \times 100 \quad (3)$$

The residual ratios of urolithin A in the urolithin A-containing aqueous solution measured after the one week of storage and after the two weeks of storage under a temperature condition of 60° C. are shown in Table 2. As shown in Table 2, it could be confirmed that stability of urolithin A increases in the presence of collagen.

TABLE 2

| | | | | Urolithin A residual ratio (%) (60° C.) | |
|---|---|---|---|---|---|
| Ethanol (%) | Glycerin (%) | Urolithin A (%) | Collagen (%) | 1 week later | 2 weeks later |
| 10 | 10 | 0.005 | 0 | 66.9 | 45.0 |
| 10 | 10 | 0.005 | 0.5 | 92.4 | 92.2 |

INDUSTRIAL APPLICABILITY

A urolithin-containing aqueous solution having improved stability and containing useful urolithin, or a dried solid product thereof, can be used for providing cosmetics, quasi drugs, medical products, sanitary articles, pharmaceuticals, foods, supplements, and the like. These are used for anti-oxidation, anti-inflammation, anti-saccharification, and/or the like.

The invention claimed is:

1. A urolithin-containing aqueous solution containing urolithin and collagen, wherein the total amount of collagen is 0.1 to 100,000 parts by weight with respect to a total amount of 1 part by weight of urolithin.

2. The aqueous solution according to claim 1, wherein the urolithin is urolithin A.

3. A dried solid composition of the aqueous solution according to claim 1.

4. A method for producing a urolithin-containing aqueous solution, the method comprising:

a blending step of blending urolithin with collagen.

5. The production method according to claim 4, wherein the collagen is at least one selected from the group consisting of type I collagen, type II collagen, type III collagen, type IV collagen, and type V collagen.

6. The production method according to claim 4, wherein the urolithin is urolithin A.

7. The production method according to claim 4, wherein the total amount of collagen is 0.1 to 100,000 parts by weight with respect to a total amount of 1 part by weight of urolithin.

8. A method for producing a dried solid composition of a urolithin-containing aqueous solution, the method comprising:

a blending step of blending urolithin with collagen; and a drying step of drying the urolithin-containing aqueous solution obtained by the blending step.

9. A stabilization method for urolithin in a urolithin-containing aqueous solution, the method comprising:

a blending step of blending urolithin with collagen, wherein the total amount of collagen is 0.1 to 100,000 parts by weight with respect to a total amount of 1 part by weight of urolithin.

10. The stabilization method according to claim 9, wherein the urolithin is urolithin A.

* * * * *